US009575033B1

(12) United States Patent
Georgeson et al.

(10) Patent No.: US 9,575,033 B1
(45) Date of Patent: Feb. 21, 2017

(54) QUANTIFICATION OF WRINKLES IN COMPOSITE OBJECTS (71) Applicant: The Boeing Company, Chicago, IL (US)

(72) Inventors: Gary E. Georgeson, Tacoma, WA (US); William Joseph Tapia, Graham, WA (US); Michael D. Fogarty, Auburn, WA (US); Hong Hue Tat, Redmond, WA (US); Richard H. Bossi, Renton, WA (US); Robert L. Carlsen, Kent, WA (US)

(73) Assignee: THE BOEING COMPANY, Chicago, IL (US)

( * ) Notice: Subject to any disclaimer, the term of this patent is extended or adjusted under 35 U.S.C. 154(b) by 606 days.

(21) Appl. No.: 14/049,974

(22) Filed: Oct. 9, 2013

(51) Int. Cl.
G01N 29/04 (2006.01)
G01N 17/00 (2006.01)
G01N 29/07 (2006.01)

(52) U.S. Cl.
CPC .............. G01N 29/04 (2013.01); G01N 29/07 (2013.01); G01N 2291/011 (2013.01); G01N 2291/0231 (2013.01); G01N 2291/102 (2013.01)

(58) Field of Classification Search
CPC ...... G01N 29/043; G01N 29/07; G01N 29/11; G01N 29/4472; G01N 2291/102; G01N 2291/0231; G01N 2291/2694

USPC ..... 702/39, 42, 66, 155, 159; 73/598, 865.8; 382/141
See application file for complete search history.

(56) References Cited

U.S. PATENT DOCUMENTS

| 5,554,808 | A | * | 9/1996 | Chiao | G01N 29/07 73/598 |
| 8,332,165 | B1 | | 12/2012 | Tae et al. | |
| 2004/0031337 | A1 | * | 2/2004 | Masaniello | F17D 5/02 73/865.8 |
| 2013/0188858 | A1 | | 7/2013 | Lin et al. | |

OTHER PUBLICATIONS

Wu et al., "Methods and Systems for Inspection of Composite Irregularities," U.S. Appl. No. 13/891,688, filed May 10, 2013, 21 pages.
Greegor et al., "Methods and Systems for Inspection of Composite Irregularities," U.S. Appl. No. 13/928,870, filed Jun. 27, 2013, 22 pages.

* cited by examiner

Primary Examiner — John H Le
(74) Attorney, Agent, or Firm — Yee & Associates, P.C.

(57) ABSTRACT

A method and apparatus for evaluating an object having a wrinkle. Energy is sent into the object at a plurality of locations using an array of transmitting elements. Reflected energy is received at an array of receiving elements in response to a portion of the energy being reflected off a plurality of layers in the object. A three-dimensional model of the wrinkle in the object is created based on the reflected energy received at the array of receiving elements.

18 Claims, 8 Drawing Sheets

QUANTIFICATION OF WRINKLES IN COMPOSITE OBJECTS

BACKGROUND INFORMATION

1. Field

The present disclosure relates generally to wrinkles in composite objects and, in particular, to evaluating the wrinkles in composite objects. Still more particularly, the present disclosure relates to a method and apparatus for generating three-dimensional data about a wrinkle in a composite object using an ultrasonic inspection system.

2. Background

A composite object may be comprised of multiple layers. These layers are oftentimes referred to as composite plies. In some cases, a wrinkle may form within a composite object. The wrinkle may be formed by a ridge, a furrow, and/or a crease in one or more layers of a portion of the composite object. A wrinkle in a composite object may reduce one or more of the mechanical properties of the composite object. For example, without limitation, a wrinkle may reduce the stiffness of a composite object at or near the location of the wrinkle.

Different types of inspection systems may be used to detect wrinkles in composite objects. For example, an ultrasonic inspection system may be used to identify a wrinkle in a composite object. However, some currently available ultrasonic inspection systems may be unable to quantify certain properties about a wrinkle in a composite object. As one illustrative example, some currently available ultrasonic inspection systems may be unable to measure the actual shape or size of a wrinkle. In particular, these ultrasonic inspection systems may be unable to measure the shape or size of a wrinkle in three dimensions.

The shape and size of a wrinkle in a composite object may determine how the wrinkle affects the mechanical properties of the composite object. When the shape and size of a wrinkle in a composite object cannot be quantified, the wrinkle may need to be assumed a "worst-case" scenario. The composite object may then need to be discarded or reworked even if the wrinkle actually has a shape and size within selected tolerances. Therefore, it would be desirable to have a method and apparatus that take into account at least some of the issues discussed above, as well as other possible issues.

SUMMARY

In one illustrative example, a method is provided for evaluating an object. Energy is sent into the object at a plurality of locations using an array of transmitting elements. Reflected energy is received at an array of receiving elements in response to a portion of the energy being reflected off a plurality of layers in the object. A three-dimensional model of a wrinkle in the object is created based on the reflected energy received at the array of receiving elements.

In another illustrative embodiment, an apparatus comprises an array of transmitting elements, an array of receiving elements, and a model generator. The array of transmitting elements is configured to send energy into a plurality of locations on an object. The array of receiving elements is configured to receive at least a portion of the energy that is reflected off the object as reflected energy. The model generator is configured to create a three-dimensional model of a wrinkle in the object based on the reflected energy.

In yet another illustrative embodiment, an ultrasonic inspection system comprises an array of transmitting elements, an array of receiving elements, and a model generator. The array of transmitting elements is configured to send an ultrasonic beam into a composite object at each of a plurality of locations on the object using a transmitting portion of the array of transmitting elements. The array of receiving elements is configured to receive a plurality of reflected signals corresponding to the plurality of layers in the composite object in response to the ultrasonic beam being sent into the composite object at a location in the plurality of locations. The model generator is configured to create a three-dimensional model of the wrinkle in the composite object based on the plurality of reflected signals received for each location in the plurality of locations. The three-dimensional model is used to determine a size and a shape of the wrinkle.

The features and functions can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the illustrative embodiments are set forth in the appended claims. The illustrative embodiments, however, as well as a preferred mode of use, further objectives and features thereof, will best be understood by reference to the following detailed description of an illustrative embodiment of the present disclosure when read in conjunction with the accompanying drawings, wherein:

DETAILED DESCRIPTION

The illustrative embodiments recognize and take into account different considerations. For example, the illustrative embodiments recognize and take into account that it may be desirable to have a method and apparatus capable of quantifying the shape and size of a wrinkle in a composite object.

Further, the illustrative embodiments recognize and take into account that the layers of a composite object may be arranged substantially parallel to a plane. However, when a wrinkle is present in a portion of the composite object, one or more of the layers of the composite object may be raised or lowered outside this plane. In this manner, the wrinkle may be referred to as an "out-of-plane" wrinkle. The illustrative embodiments recognize and take into account that a phased array ultrasonic inspection system may be used to quantify the shapes and sizes of wrinkles.

Figure 1:
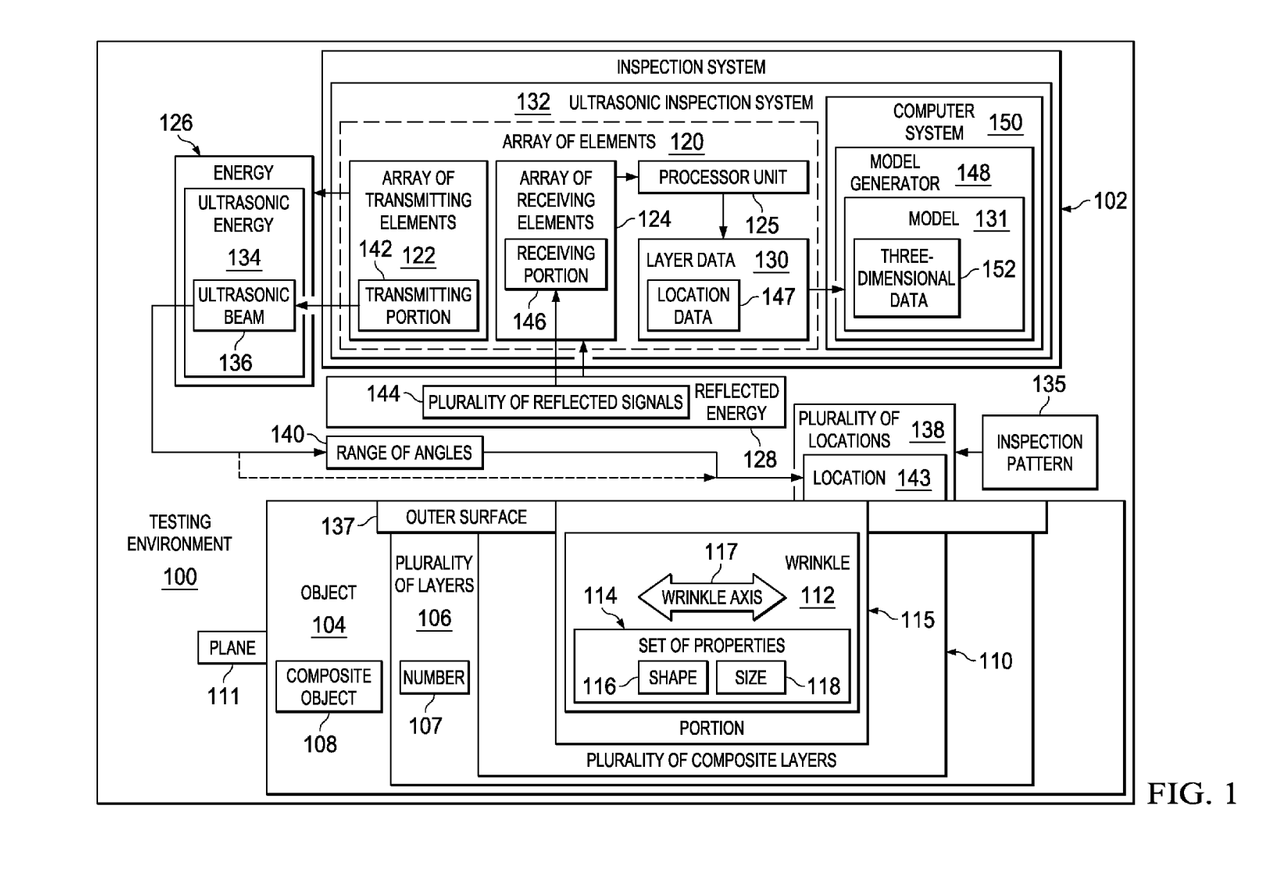
FIG. 1 is an illustration of a testing environment in the form of a block diagram in accordance with an illustrative embodiment.

Referring now to the figures and, in particular, with reference to FIG. 1, an illustration of a testing environment is depicted in the form of a block diagram in accordance with an illustrative embodiment. In this illustrative example, testing environment 100 may be an environment in which inspection system 102 may be used to evaluate object 104.

As depicted, object 104 may be any object comprised of plurality of layers 106. Number 107 is the number of layers in plurality of layers 106. In one illustrative example, object 104 takes the form of composite object 108. When object 104 is composite object 108, plurality of layers 106 may be referred to as plurality of composite layers 110. Plurality of composite layers 110 may also be referred to as a plurality of plies or composite plies in some cases. Each of plurality of composite layers 110 may be comprised of composite material.

In one illustrative example, object 104 may be substantially planar. In other words, plurality of layers 106 that form object 104 may be arranged substantially parallel to plane 111. However, in some cases, wrinkle 112 may be present or develop within object 104. Wrinkle 112 may be formed by, for example, a ridge, a furrow, and/or a crease in one or more of plurality of layers 106.

Inspection system 102 may be used to evaluate wrinkle 112. In particular, inspection system 102 may be used to quantify set of properties 114 about wrinkle 112. As used herein, a "set of" items may be one or more items. For example, set of properties 114 may include one or more properties. In this illustrative example, set of properties 114 includes shape 116 and size 118 of wrinkle 112.

In one illustrative example, a different type of inspection system may first be used to identify portion 115 of object 104 that includes wrinkle 112 and identify wrinkle axis 117. Portion 115 of object 104 identified may depend on shape 116 and size 118 of wrinkle 112. Portion 115 may be identified such that portion 115 includes all of wrinkle 112 as well as some of the unwrinkled portion of object 104 around wrinkle 112.

Wrinkle 112 may extend substantially linearly, within tolerances, in a direction substantially parallel to plane 111. Wrinkle axis 117 is identified as the axis in the direction in which wrinkle 112 extends.

Inspection system 102 may be used to inspect portion 115 of object 104 to quantify shape 116 and size 118 of wrinkle 112. As depicted, inspection system 102 may include array of transmitting elements 122, array of receiving elements 124, and processor unit 125. In some cases, array of transmitting elements 122 and array of receiving elements 124 may be implemented as separate arrays. However, in other cases, array of transmitting elements 122 and array of receiving elements 124 may be implemented as a same array of elements 120. In other words, array of elements 120 may be configured for use in both transmitting and receiving. Array of elements 120 may be implemented as an array of transducers.

In this illustrative example, array of transmitting elements 122 may include two or more elements arranged in a row. In this manner, array of transmitting elements 122 may be a linear array of transmitting elements. Similarly, array of receiving elements 124 may include two or more elements arranged in a row. In this manner, array of receiving elements 124 may be a linear array of receiving elements.

Array of transmitting elements 122 may be configured to send energy 126 into object 104. Array of receiving elements 124 may be configured to receive reflected energy 128. Reflected energy 128 may be the portion of energy 126 sent into object 104 that is reflected off the surface of each of plurality of layers 106.

In one illustrative example, inspection system 102 takes the form of ultrasonic inspection system 132. When inspection system 102 takes the form of ultrasonic inspection system 132, energy 126 sent into object 104 is ultrasonic energy 134.

Ultrasonic inspection system 132 may be placed over outer surface 137 of portion 115 of object 104. In this illustrative example, ultrasonic inspection system 132 may be placed over outer surface 137 such that array of transmitting elements 122 directly contacts outer surface 137. However, in other illustrative examples, ultrasonic inspection system 132 may be placed over outer surface 137 such that array of transmitting elements 122 does not directly contact outer surface 137.

Ultrasonic inspection system 132 is then operated to send ultrasonic energy 134 into object 104 at plurality of locations 138 on outer surface 137 of portion 115 of object 104. More specifically, ultrasonic inspection system 132 sends ultrasonic energy 134 in the form of ultrasonic beam 136 into object 104 at each location in plurality of locations 138.

In one illustrative example, plurality of locations 138 may include locations defined by a grid substantially parallel to plane 111. For example, without limitation, plurality of locations 138 may be two-dimensional locations along a grid substantially parallel to plane 111. This grid may be formed based on wrinkle axis 117 and an axis substantially perpendicular to wrinkle axis 117. Of course, in other illustrative examples, a location in plurality of locations 138 may be a three-dimensional location such as, for example, without limitation, a location in x, y, and z coordinates relative to object 104.

Ultrasonic inspection system 132 may be moved over outer surface 137 of portion 115 of object 104 to the different locations in plurality of locations 138 according to inspection pattern 135.

Inspection pattern 135 may be, for example, without limitation, a raster pattern. When inspection pattern 135 takes the form of a raster pattern, ultrasonic beam 136 is sent into object 104 at each location in plurality of locations 138, one location at a time. Of course, in other examples, inspection pattern 135 may take some other form.

Ultrasonic beam 136 may be formed by using array of transmitting elements 122 in a phased manner. In particular, transmitting portion 142 of array of transmitting elements 122 may be used to form ultrasonic beam 136. Transmitting portion 142 may include one or more transmitting elements of array of transmitting elements 122. In this manner, transmitting portion 142 may include one, some, or all of array of transmitting elements 122.

In some cases, the same one or more of array of transmitting elements 122 may be used as transmitting portion 142 for sending ultrasonic beam 136 into each location in plurality of locations 138. In other cases, different portions of array of transmitting elements 122 may be used as transmitting portion 142 for sending ultrasonic beam 136 into different locations in plurality of locations 138.

In one illustrative example, each of the transmitting elements in transmitting portion 142 may be configured to transmit an ultrasonic pulse at a selected time. This time may be the same or different for the different transmitting elements in transmitting portion 142, depending on the implementation. The times at which the transmitting elements in transmitting portion 142 transmit ultrasonic pulses and the strengths of these ultrasonic pulses may be selected such that the waves formed by these ultrasonic pulses combine to form a single wavefront that travels at a selected angle relative to object 104. This single wave front forms ultrasonic beam 136. In this manner, array of transmitting elements 122 may be used to electronically steer ultrasonic beam 136 relative to object 104.

For example, ultrasonic beam 136 may be sent into object 104 at location 143 and propagated through object 104. As ultrasonic beam 136 propagates through object 104, at least a portion of ultrasonic beam 136 is reflected off the surfaces of plurality of layers 106 of object 104. These reflections, which may also be referred to as reflected ultrasonic energy, may be received by receiving portion 146 of array of receiving elements 124. Receiving portion 146 may include one or more of array of receiving elements 124. In this manner, receiving portion 146 may include one, some, or all of array of receiving elements 124.

For each layer in plurality of layers 106, the ultrasonic energy in ultrasonic beam 136 reflected off the surface of that layer is received by at least one receiving element in array of receiving elements 124. The receiving element that receives the highest-amplitude reflection is identified as receiving the reflected signal corresponding to that layer and location 143. In other words, the reflected signal corresponding to a layer in plurality of layers 106 is a maximum reflection off the surface of the layer that is received at a receiving element in array of receiving elements 124. In this manner, receiving portion 146 may receive plurality of reflected signals 144 off plurality of layers 106 in response to ultrasonic beam 136 being sent into object 104 at location 143.

In this illustrative example, plurality of reflected signals 144 may include a reflection off each of plurality of layers 106. However, in other illustrative examples, plurality of reflected signals 144 may include reflections off only some of plurality of layers 106.

Each receiving element in receiving portion 146 that receives a reflection may convert that reflection into an electrical signal. Processor unit 125 may be configured to receive the electrical signal formed by each receiving element in receiving portion 146 and convert the electrical signal into data that is processed to form location data 147 for location 143.

Location data 147 may include, for example, an amplitude and time for each of plurality of reflected signals 144 received for location 143. The amplitude may be the amplitude of the reflected signal, while the time may be the time of arrival of the reflected signal. In some cases, this time of arrival may be with respect to the time at which ultrasonic beam 136 was sent into object 104. In one illustrative example, location data 147 includes a data point for each of plurality of reflected signals 144 received in response to ultrasonic beam 136 being sent into object 104 at location 143. The data point for a reflected signal includes at least one of an amplitude value, a time value, an element identifier, a transmitting angle for that reflected signal, or some other type of value.

As used herein, the phrase "at least one of," when used with a list of items, means different combinations of one or more of the listed items may be used and only one of the items in the list may be needed. The item may be a particular object, thing, or category. In other words, "at least one of" means any combination of items or number of items may be used from the list, but not all of the items in the list may be required.

For example, "at least one of item A, item B, and item C" may mean item A; item A and item B; item B; item A, item B, and item C; or item B and item C. In some cases, "at least one of item A, item B, and item C" may mean, for example, without limitation, two of item A, one of item B, and ten of item C; four of item B and seven of item C; or some other suitable combination.

The element identifier identifies the receiving element in array of receiving elements 124 that received the reflected signal. The transmitting angle is the angle at which ultrasonic beam 136 was sent into object 104 that resulted in a reflected signal.

Location data 147 for each location in plurality of locations 138 is collected to form layer data 130 for portion 115 of object 104. Processor unit 125 generates layer data 130 for portion 115 of object 104 as portion 115 is being scanned. Portion 115 of object 104 may be considered "fully scanned" once ultrasonic beam 136 has been sent into each location in plurality of locations 138 on portion 115 of object 104.

In these illustrative examples, ultrasonic beam 136 is sent into object 104 at a same selected angle relative to plane 111 at each location in plurality of locations 138. However, in other illustrative examples, ultrasonic beam 136 may be electronically steered to sweep through range of angles 140 relative to plane 111 at each location in plurality of locations 138. Range of angles 140 may be the same or different for locations in plurality of locations 138.

For example, range of angles 140 may be a range of about 160 degrees. Of course, in other examples, range of angles 140 may be some other range. The maximum range may be about 180 degrees. For location 143, ultrasonic beam 136 may be swept perpendicularly to plane 111 through object 104 from about 10 degrees to about 170 degrees relative to plane 111 and location 143. With this type of method, for each layer in plurality of layers 106, processor unit 125 identifies the highest-amplitude reflection off that layer within range of angles 140 as the reflected signal corresponding to that layer and location 143. Location data 147 for location 143 in this example includes the amplitude value, the time value, the element identifier, and the transmitting angle for the reflected signal received from each of plurality of layers 106.

Processor unit 125 may be configured to send layer data 130 to model generator 148 for processing. Model generator 148 uses layer data 130 to generate model 131. In this illustrative example, model 131 comprises three-dimensional data 152 about wrinkle 112. In this manner, model 131 may be a three-dimensional model. Three-dimensional data 152 may be used to quantify shape 116 and size 118 of wrinkle 112.

Layer data 130 may be processed to generate three-dimensional data 152 by identifying a depth for each layer in plurality of layers 106 at each location in plurality of locations 138. The depth for a layer at a particular location is the depth of the surface of that layer relative to outer surface 137 of object 104 or relative to array of transmitting elements 122 at the particular location.

As one illustrative example, the depth of a layer in plurality of layers 106 at location 143 may be identified based on the time value and the element identifier in location data 147 for location 143. The element identifier in location data 147 for location 143 is used to identify the angle of reflection for the reflected signal received at the receiving element identified by the element identifier. The angle of reflection may be the angle of the reflected signal relative to the angle at which ultrasonic beam 136 is sent into object 104 at location 143 or relative to plane 111. The time value and the angle of reflection are then used to identify the depth.

Three-dimensional data 152 allows wrinkle 112 to be quantified such that the actual shape 116 and size 118 of wrinkle 112 can be determined within selected tolerances. Model 131 of object 104 with wrinkle 112 may be used to perform, for example, a stress analysis of object 104 having wrinkle 112. By using model 131 that defines shape 116 and size 118 of wrinkle 112 in performing this stress analysis, the impact of wrinkle 112 on the mechanical properties of object 104 may be more accurately determined. For example, the impact of wrinkle 112 on the stiffness of object 104 may be more accurately determined.

Model generator 148 may be implemented using hardware, software, firmware, or a combination thereof. When software is used, the operations performed by model generator 148 may be implemented using, for example, without limitation, program code configured to run on a processor unit, such as processor unit 804 illustrated below in FIG. 8. When firmware is used, the operations performed by model generator 148 may be implemented using, for example, without limitation, program code and data and may be stored in persistent memory to run on the processor unit.

When hardware is employed, the hardware may include one or more circuits that operate to perform the operations performed by model generator 148. Depending on the implementation, the hardware may take the form of a circuit system, an integrated circuit, an application specific integrated circuit (ASIC), a programmable logic device, or some other suitable type of hardware device configured to perform any number of operations.

A programmable logic device may be configured to perform certain operations. The device may be permanently configured to perform these operations or may be reconfigurable. A programmable logic device may take the form of, for example, without limitation, a programmable logic array, a programmable array logic, a field programmable logic array, a field programmable gate array, or some other type of programmable hardware device.

In some illustrative examples, the operations and/or processes performed by model generator 148 may be performed using organic components integrated with inorganic components. In some cases, the operations and/or processes may be performed entirely by organic components, excluding a human being. As one illustrative example, circuits in organic semiconductors may be used to perform these operations and/or processes.

In this illustrative example, model generator 148 is implemented within computer system 150. Computer system 150 may be comprised of one or more computers. When more than one computer is present in computer system 150, these computers may be in communication with each other. Model generator 148 and computer system 150 are considered part of ultrasonic inspection system 132. However, in other illustrative examples, at least some portion of model generator 148 and/or computer system 150 may be considered separate from ultrasonic inspection system 132. For example, without limitation, at least a portion of model generator 148 may be implemented remotely.

The illustration of testing environment 100 in FIG. 1 is not meant to imply physical or architectural limitations to the manner in which an illustrative embodiment may be implemented. Other components in addition to or in place of the ones illustrated may be used. Some components may be optional. Also, the blocks are presented to illustrate some functional components. One or more of these blocks may be combined, divided, or combined and divided into different blocks when implemented in an illustrative embodiment.

In some illustrative examples, the operations performed by model generator 148 may be implemented within processor unit 125. Processor unit 125 may then be configured to send model 131 to other computer systems for processing. In other illustrative examples, layer data 130 may be generated by model generator 148 or some other type of unit within computer system 150 based on raw data received from array of receiving elements 124. For example, the electrical signals generated by array of receiving elements 124 may be received directly at computer system 150.

Figure 2:
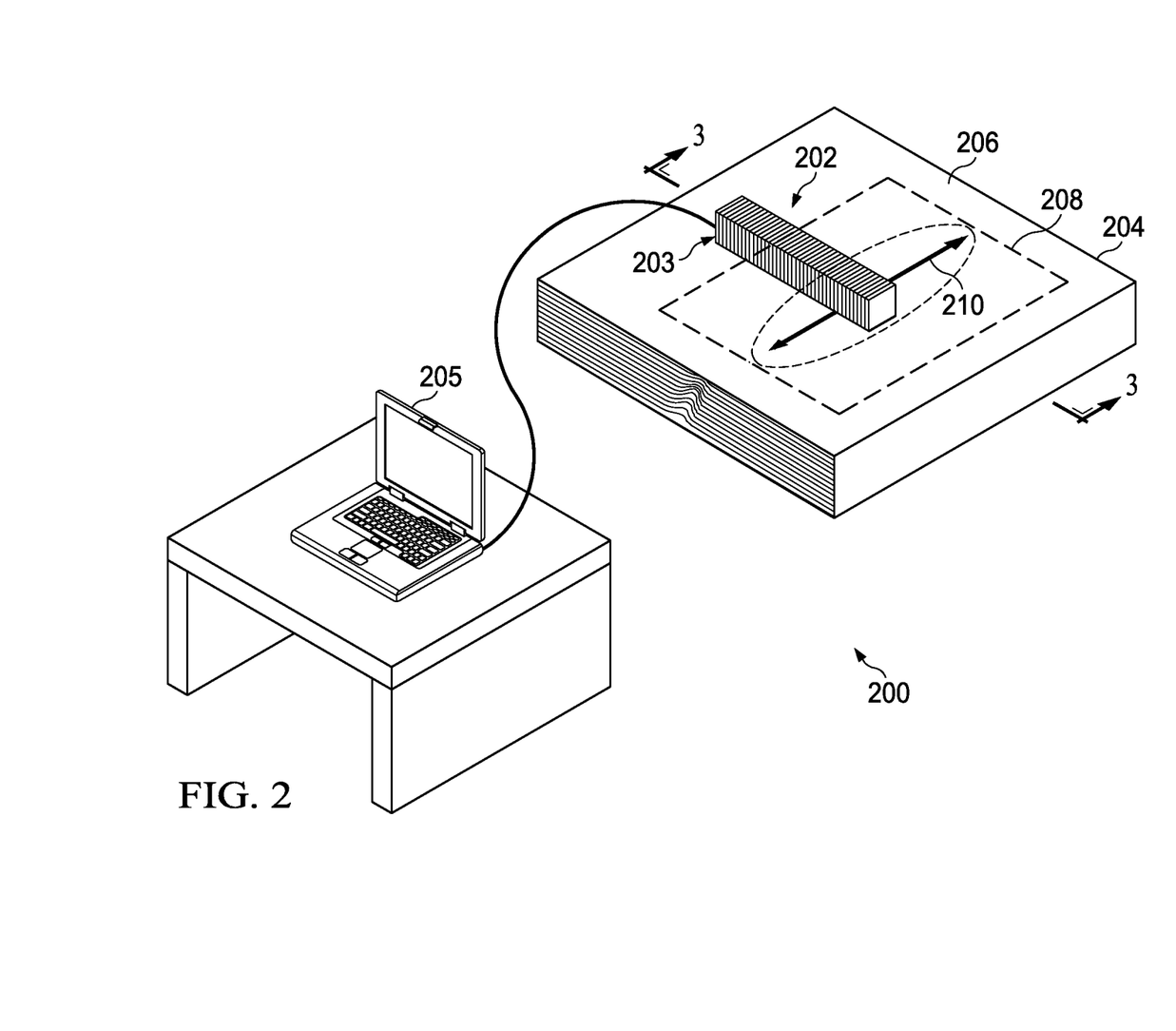
FIG. 2 is an illustration of a testing environment in accordance with an illustrative embodiment.

With reference now to FIG. 2, an illustration of a testing environment is depicted in accordance with an illustrative embodiment. In this illustrative example, testing environment 200 may be an example of one implementation for testing environment 100 in FIG. 1. As depicted, in testing environment 200, ultrasonic inspection system 202 is depicted. Ultrasonic inspection system 202 is an example of one implementation for ultrasonic inspection system 132 in FIG. 1.

As depicted, ultrasonic inspection system 202 includes of array of elements 203 and computer system 205. Array of elements 203 is configured to function as both an array of transmitting elements and an array of receiving elements. In this manner, array of elements 203 may be an example of one implementation for array of elements 120 in FIG. 1. In this illustrative example, array of elements 203 has been positioned over outer surface 206 of composite object 204.

Composite object 204 may be an example of one implementation for composite object 108 in FIG. 1. In this illustrative example, composite object 204 comprises composite layers. A wrinkle in these composite layers has been generally detected within portion 208 of composite object 204. Further, the wrinkle has been identified as extending linearly along wrinkle axis 210. Ultrasonic inspection system 202 may be used to inspect portion 208 of composite object 204 such that the shape and size of the wrinkle may be quantified.

In this illustrative example, array of elements 203 is configured to send an ultrasonic beam into composite object 204 at each of a plurality of locations preselected such that portion 208 of composite object 204 may be raster scanned. Reflected energy that is reflected off the surfaces of the layers in composite object 204 are received by array of elements 203 and converted into electrical signals that are then sent to computer system 205 for processing.

Figure 3:
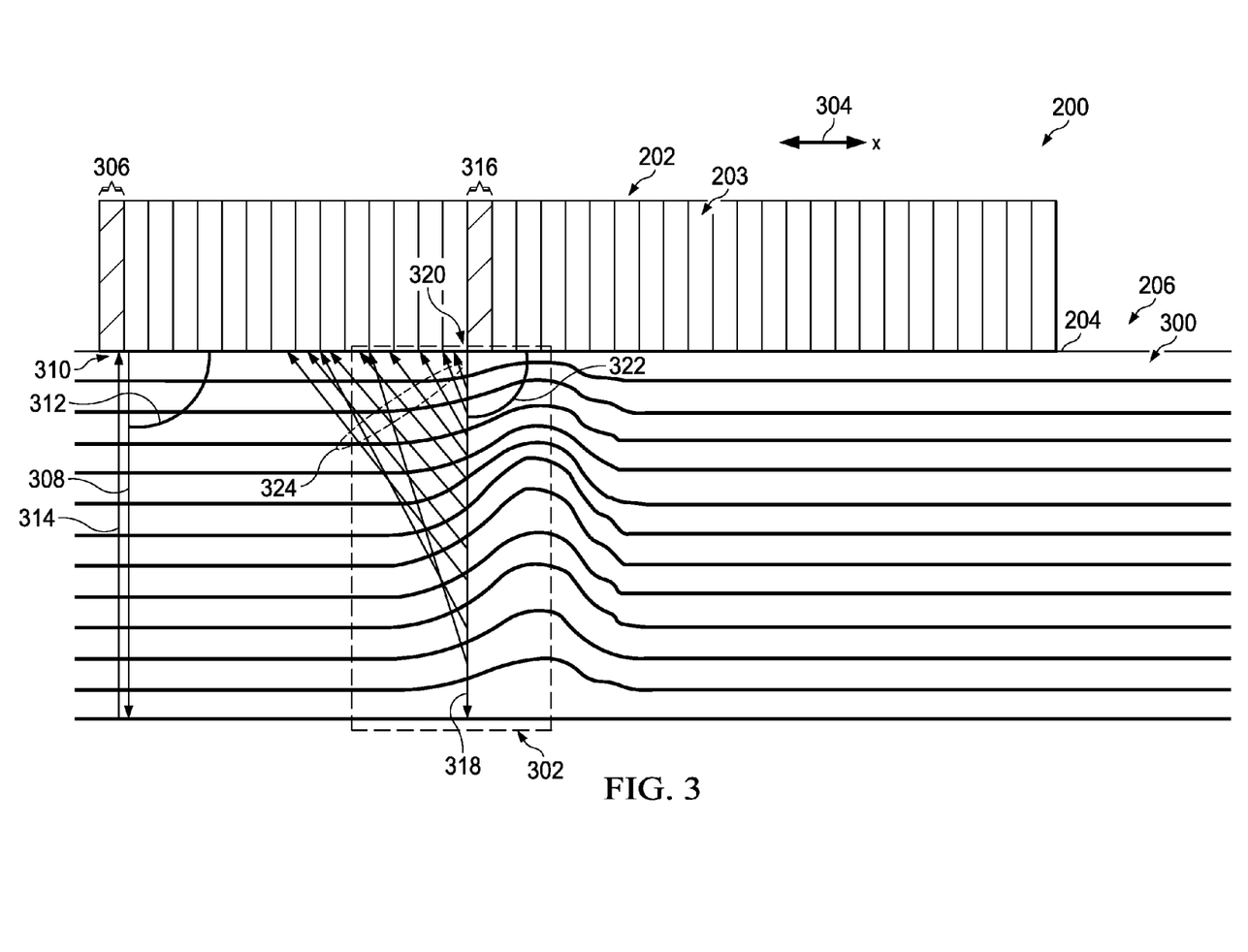
FIG. 3 is an illustration of a cross-sectional view of a composite object in accordance with an illustrative embodiment.

With reference now to FIG. 3, an illustration of a cross-sectional view of composite object 204 from FIG. 2 is depicted in accordance with an illustrative embodiment. In this illustrative example, a cross-sectional view of composite object 204 from FIG. 2 is taken with respect to lines 3-3 in FIG. 2. As depicted, composite object 204 is comprised of plurality of layers 300. Plurality of layers 300 may be an example of one implementation for plurality of layers 106 in FIG. 1.

As depicted, composite object 204 has wrinkle 302. Wrinkle 302 is an example of one implementation for wrinkle 112 in FIG. 1. Wrinkle 302 is formed by a portion of plurality of layers 300. Wrinkle 302 may extend linearly in a direction along wrinkle axis 210 from FIG. 2, which extends through the page in FIG. 3.

In this illustrative example, the individual elements in array of elements 203 may be more clearly seen. Array of elements 203 is an array of ultrasonic transducers in the form of a linear array of ultrasonic transducers configured to send and receive ultrasonic energy. Array of elements 203 may be configured to send energy into composite object 204 and receive reflected energy.

As depicted, array of elements 203 is positioned over wrinkle 302 in the direction of x-axis 304, which may be substantially perpendicular to wrinkle axis 210 in FIG. 2. In this illustrative example, element 306 of array of elements 203 is used to form ultrasonic beam 308 and send ultrasonic beam 308 into composite object 204. Element 306 and ultrasonic beam 308 may be examples of implementations for transmitting portion 142 and ultrasonic beam 136, respectively, in FIG. 1.

In response to ultrasonic beam 308 propagating through composite object 204, at least a portion of ultrasonic beam 308 is reflected off the surface of each of plurality of layers 300. As depicted, ultrasonic beam 308 is sent into composite object 204 at location 310 on composite object 204 at angle 312 relative to composite object 204. Angle 312 is about 90 degrees relative to composite object 204, with respect to the plane through composite object 204. This plane may be the plane along which plurality of layers 300 lie substantially parallel.

The highest-amplitude reflections off the surfaces of plurality of layers 300 form reflected signals 314 corresponding to plurality of layers 300 at location 310. Because ultrasonic beam 308 is not directed into composite object 204 at or near wrinkle 302, reflected signals 314 are reflected back in substantially the same direction in which ultrasonic beam 308 was sent into composite object 204.

One or more elements in array of elements 203 may receive reflected signals 314. As depicted, element 306 receives reflected signals 314 because reflected signals 314 are reflected back in the same direction in which ultrasonic beam 308 was sent into composite object 204. An amplitude and time are generated for each reflected signal received at element 306.

Thereafter, a new location on composite object 204 may be tested by choosing a different portion of array of elements 203 to send an ultrasonic signal into composite object 204. For example, element 316 in array of elements 203 may be used to send ultrasonic beam 318 into composite object 204 at location 320 on composite object 204. Ultrasonic beam 318 may be sent into composite object 204 at angle 322 relative to composite object 204, which may be about 90 degrees relative to composite object 204.

In response to ultrasonic beam 318 propagating through composite object 204, reflected signals 324 are reflected off the surfaces of plurality of layers 300 and received by array of elements 203. As depicted, wrinkle 302 may cause reflected signals 324 to be received by different elements within array of elements 203.

In this manner, different portions of array of elements 203 may be used to send an ultrasonic signal into composite object 204 at different locations on composite object 204. Although ultrasonic beam 308 and ultrasonic beam 318 are shown as being sent into composite object 204 at angles of about 90 degrees relative to composite object 204, an ultrasonic beam may be sent into composite object 204 at a different angle.

Thus, different elements in array of elements 203 may be used to send ultrasonic signals into composite object 204. Further, array of elements 203 may be moved over outer surface 206 of composite object 204 such that an ultrasonic beam is sent into composite object 204 at each of the plurality of locations preselected for inspection. In this manner, array of elements 203 may be used to evaluate composite object 204.

For a particular location at which an ultrasonic beam is sent into composite object 204, a reflected signal is identified for each layer in plurality of layers 300. The reflected signal is identified as the highest-amplitude reflection received at one of array of elements 203. The element identifier identifying this element, the amplitude of the reflected signal, and the time of arrival of the reflected signal are used to form location data for that particular location. The location data collected for each of the plurality of locations preselected for inspection collectively forms layer data that may be used to form a three-dimensional model of composite object 204 and wrinkle 302 in composite object 204.

Figure 4:
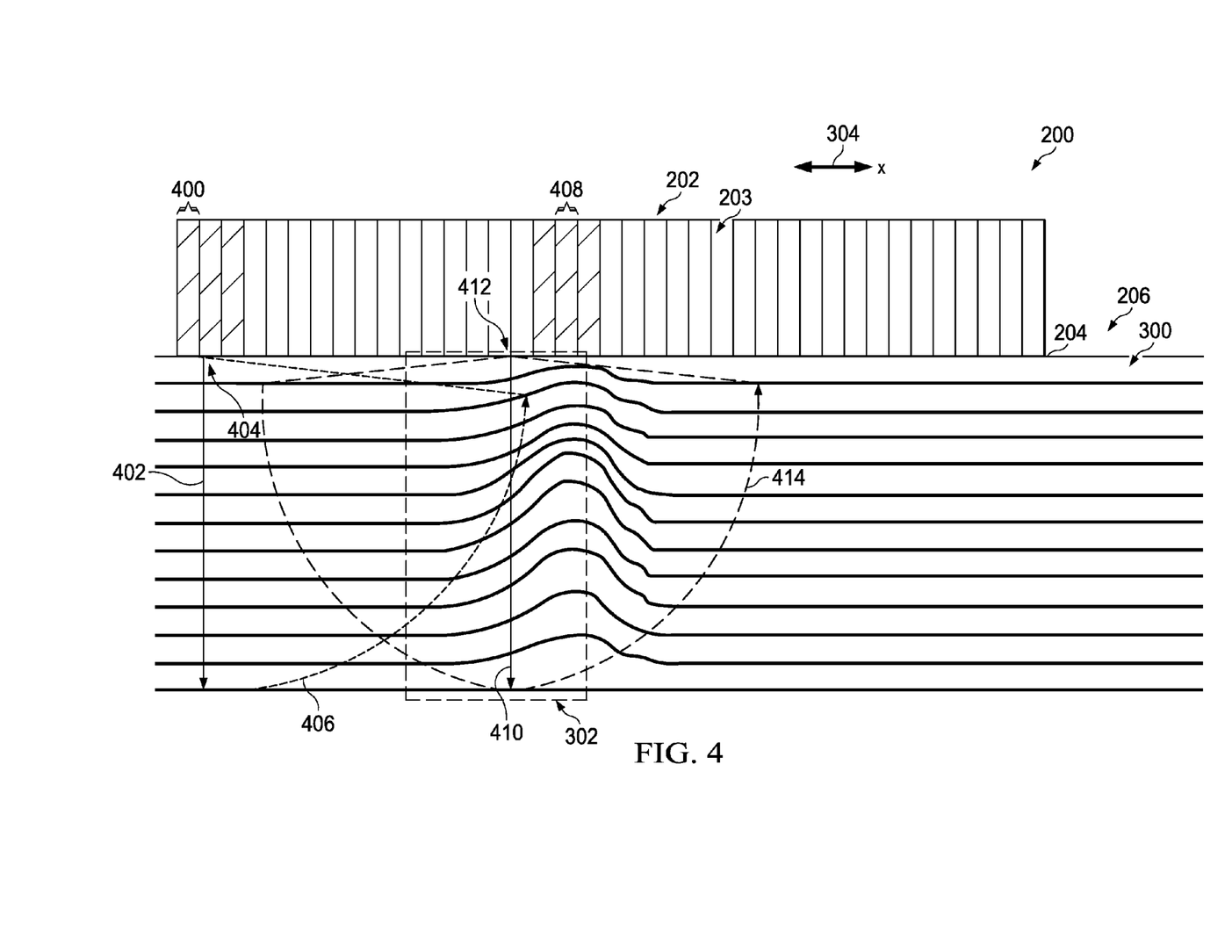
FIG. 4 is an illustration of a cross-sectional view of a composite object in accordance with an illustrative embodiment.

With reference now to FIG. 4, an illustration of the cross-sectional view of composite object 204 from FIG. 3 is depicted in accordance with an illustrative embodiment. In this illustrative example, array of elements 203 may be used to evaluate composite object 204 by electronically steering an ultrasonic beam across a range of angles at each location on composite object 204 into which the ultrasonic beam is sent.

For example, portion 400 of array of elements 203 may be used to send ultrasonic beam 402 into composite object 204 at location 404. Portion 400 is used to electronically steer ultrasonic beam 402 such that ultrasonic beam 402 sweeps across range of angles 406 relative to the plane through composite object 204.

The angle for ultrasonic beam 402 at which the highest-amplitude reflection is received at an element in array of elements 203 for each layer in plurality of layers 300 is used to identify the reflected signal corresponding to that layer. Since location 404 is not where wrinkle 302 is located, all of the reflected signals are received in the same direction. The angle of reflection, the amplitude, and the time of arrival for the reflected signal corresponding to each of plurality of layers 300 are identified to form location data for location 404.

Similarly, portion 408 of array of elements 203 may be used to send ultrasonic beam 410 into composite object 204 at location 412. Ultrasonic beam 410 is electronically steered such that ultrasonic beam 402 sweeps across range of angles 414 relative to the plane through composite object 204.

The angle for ultrasonic beam 402 at which the highest-amplitude reflection is received at an element in array of elements 203 for each layer in plurality of layers 300 is used to identify the reflected signal corresponding to that layer. Since wrinkle 302 is present at location 412, the reflected signals may be received in different directions. The angle of reflection, the amplitude, and the time of arrival for the reflected signal corresponding to each of plurality of layers 300 are identified to form location data for location 412.

Figure 5:
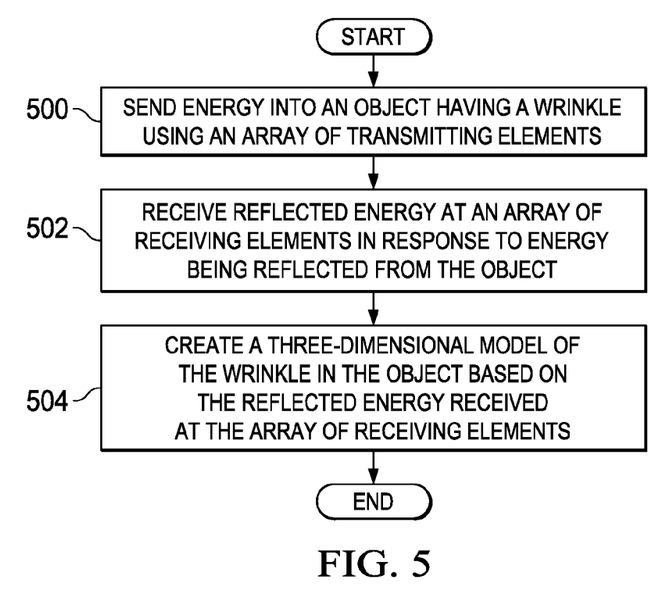
FIG. 5 is an illustration of a process for evaluating an object having a wrinkle in the form of a flowchart in accordance with an illustrative embodiment.

With reference now to FIG. 5, an illustration of a process for evaluating an object having a wrinkle is depicted in the form of a flowchart in accordance with an illustrative embodiment. The process illustrated in FIG. 5 may be implemented using inspection system 102 and model generator 148 in FIG. 1.

The process begins by sending energy into an object having a wrinkle using an array of transmitting elements (operation 500). Thereafter, reflected energy is received at an array of receiving elements in response to the energy being reflected off the object (operation 502).

Next, a three-dimensional model of the wrinkle in the object is created based on the reflected energy received at the array of receiving elements (operation 504), with the process terminating thereafter. The model created in operation 504 may comprise three-dimensional data about the wrinkle that allows the shape and size of the wrinkle to be quantified. The model of the wrinkle may be used in performing a stress analysis of the object to determine the impact of the wrinkle on the mechanical properties of the object.

Figure 6:
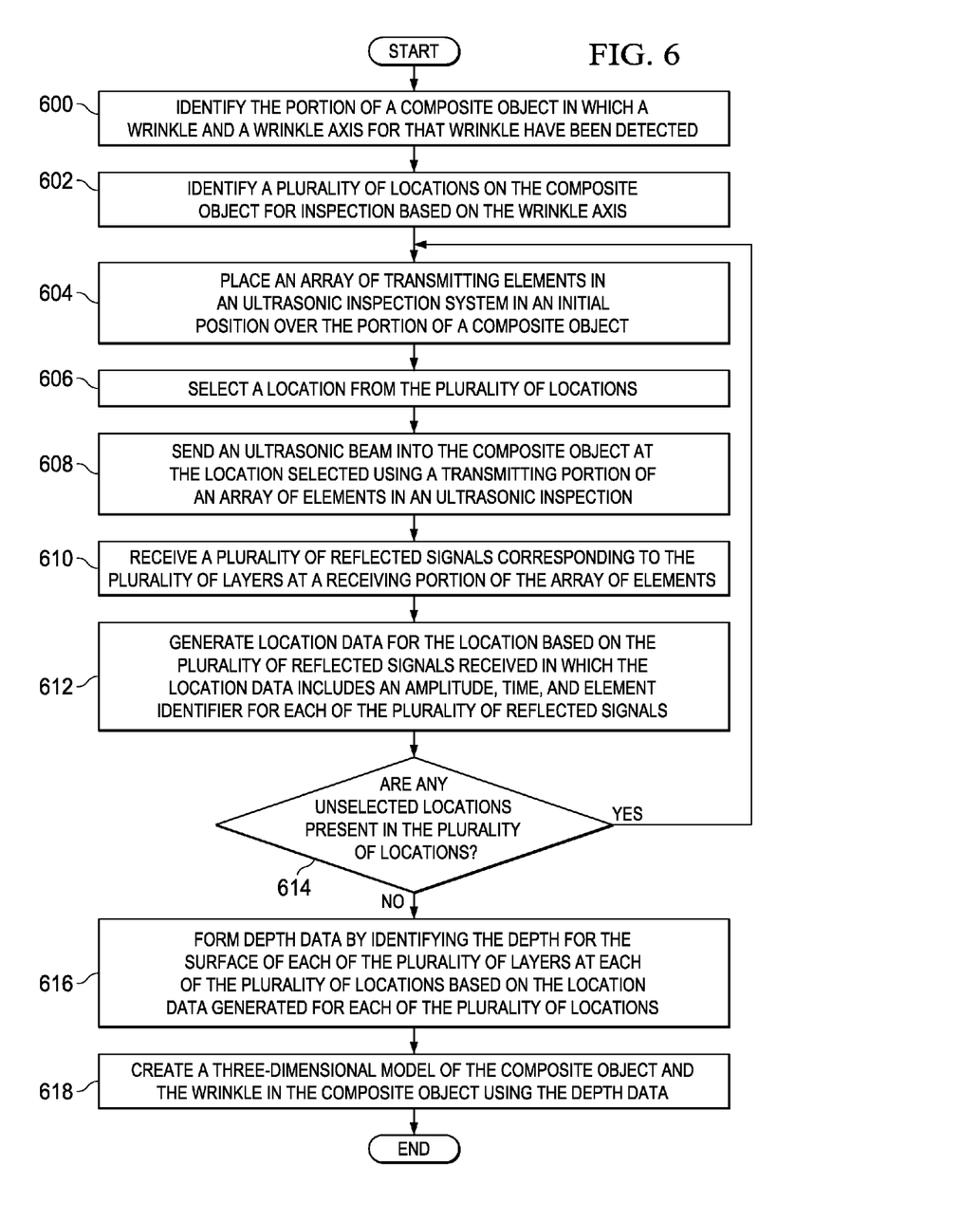
FIG. 6 is an illustration of a process for generating a model of a wrinkle in a composite object in the form of a flowchart in accordance with an illustrative embodiment.

With reference now to FIG. 6, an illustration of a process for generating a model of a wrinkle in a composite object is depicted in the form of a flowchart in accordance with an illustrative embodiment. The process illustrated in FIG. 6 may be implemented using ultrasonic inspection system 132 and model generator 148 in FIG. 1.

The process begins by identifying a portion of a composite object in which a wrinkle and a wrinkle axis for that wrinkle have been detected (operation 600). Next, a plurality of locations on the composite object is identified for inspection based on the wrinkle axis (operation 602). For example, in operation 602, the wrinkle axis may form one axis of a grid that is used to identify the plurality of locations. An array of transmitting elements in an ultrasonic inspection system is placed in an initial position over the portion of a composite object (operation 604).

Thereafter, a location is selected from the plurality of locations (operation 606). Operation 606 may be performed based on some specified inspection pattern such as, for example, without limitation, a raster pattern. An ultrasonic beam is sent into the composite object at the location selected using a transmitting portion of an array of elements in an ultrasonic inspection (operation 608). A plurality of reflected signals corresponding to the plurality of layers is received at a receiving portion of the array of elements (operation 610). The receiving portion of the array of elements may be the same as or different from the transmitting portion of the array of elements, depending on whether the wrinkle is present at the location at which the ultrasonic beam is sent into the composite object.

Location data is generated for the location based on the plurality of reflected signals received in which the location data includes an amplitude, time, and element identifier for each of the plurality of reflected signals (operation 612). Next, a determination is made as to whether any unselected locations are present in the plurality of locations (operation 614). If any unselected locations are present, the process proceeds to operation 604 as described above.

Otherwise, if no unselected locations are present, depth data is formed by identifying the depth for the surface of each of the plurality of layers at each of the plurality of locations based on the location data generated for each of the plurality of locations (operation 616). A three-dimensional model of the composite object and the wrinkle in the composite object is created using the depth data (operation 618), with the process terminating thereafter.

Figure 7:
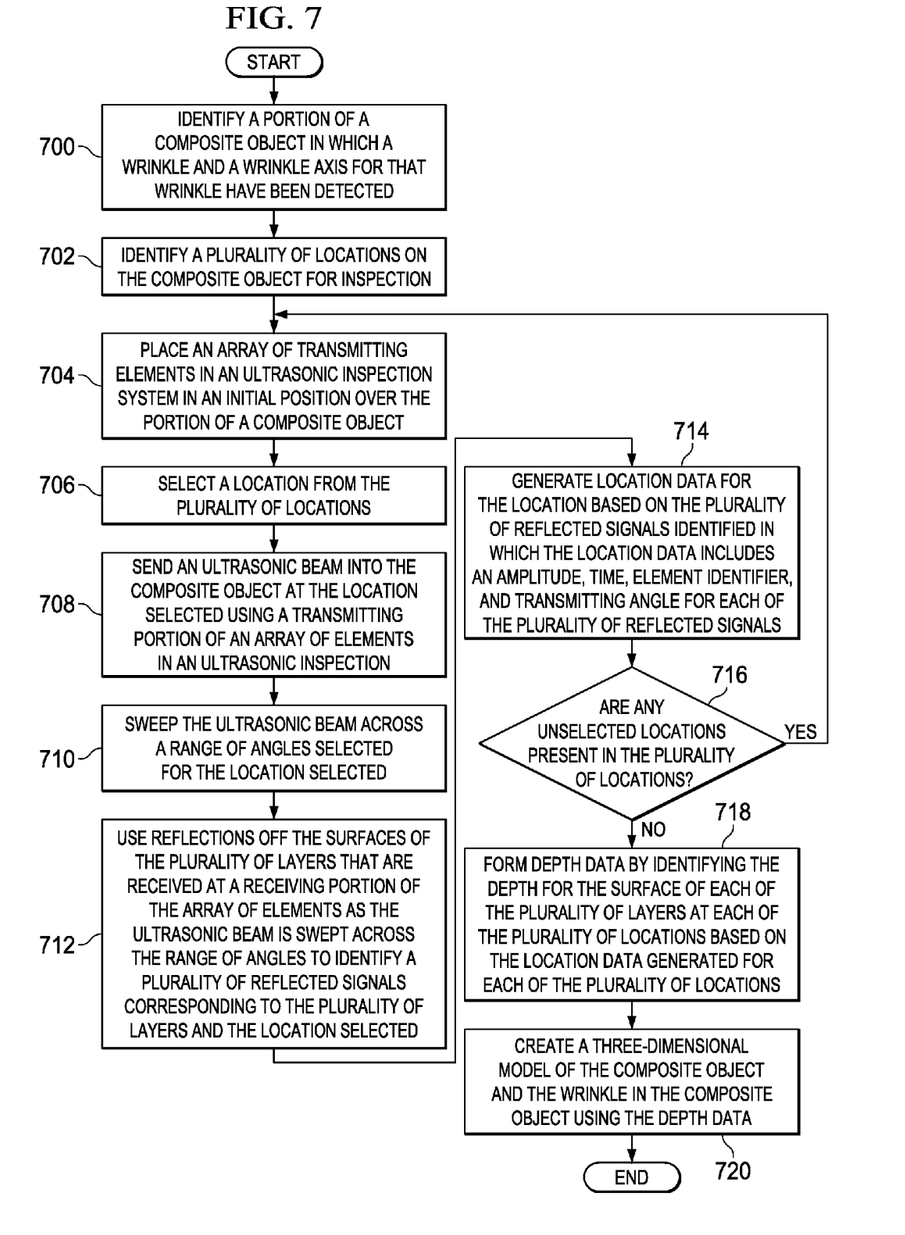
FIG. 7 is an illustration of a process for generating a model of a wrinkle in a composite object in the form of a flowchart in accordance with an illustrative embodiment.

With reference now to FIG. 7, an illustration of a process for generating a model of a wrinkle in a composite object is depicted in the form of a flowchart in accordance with an illustrative embodiment. The process illustrated in FIG. 7 may be implemented using ultrasonic inspection system 132 and model generator 148 in FIG. 1.

The process begins by identifying a portion of a composite object in which a wrinkle and a wrinkle axis for that wrinkle have been detected (operation 700). Next, a plurality of locations on the composite object is identified for inspection (operation 702). An array of transmitting elements in an ultrasonic inspection system is placed in an initial position over the portion of a composite object (operation 704).

Thereafter, a location is selected from the plurality of locations (operation 706). Operation 706 may be performed based on some specified inspection pattern such as, for example, without limitation, a raster pattern. An ultrasonic beam is sent into the composite object at the location selected using a transmitting portion of an array of elements in an ultrasonic inspection (operation 708). The ultrasonic beam is then swept across a range of angles selected for the location selected (operation 710). Reflections off the surfaces of the plurality of layers that are received at a receiving portion of the array of elements as the ultrasonic beam is swept across the range of angles are used to identify a plurality of reflected signals corresponding to the plurality of layers and the location selected (operation 712). The receiving portion of the array of elements may be the same as or different from the transmitting portion of the array of elements, depending on whether the wrinkle is present at the location at which the ultrasonic beam is sent into the composite object.

Location data is generated for the location based on the plurality of reflected signals identified in which the location data includes an amplitude, time, element identifier, and transmitting angle for each of the plurality of reflected signals (operation 714). The transmitting angle is the angle at which the ultrasonic beam was sent into the composite object that resulted in a reflected signal. Next, a determination is made as to whether any unselected locations are present in the plurality of locations (operation 716). If any unselected locations are present, the process proceeds to operation 704 as described above.

Otherwise, if no unselected locations are present, depth data is formed by identifying the depth for the surface of each of the plurality of layers at each of the plurality of locations based on the location data generated for each of the plurality of locations (operation 718). A three-dimensional model of the composite object and the wrinkle in the composite object is created using the depth data (operation 720), with the process terminating thereafter.

Figure 8:
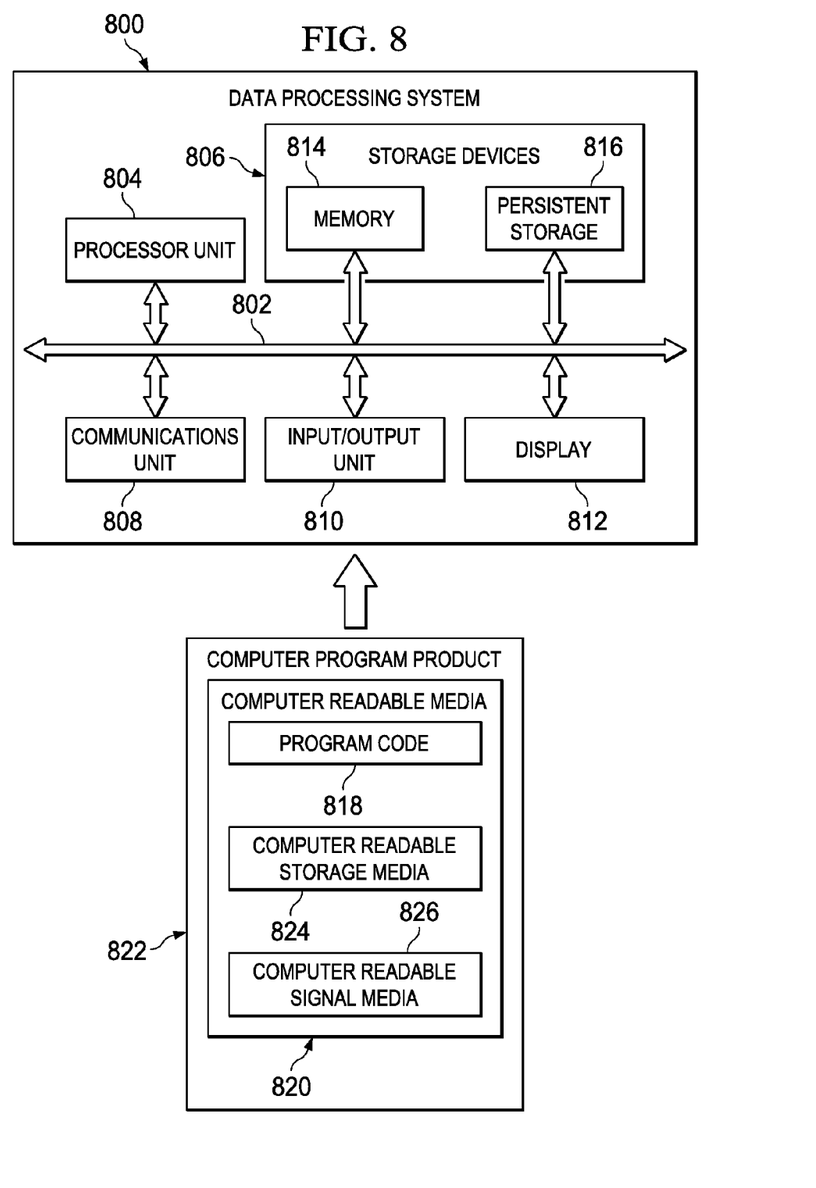
FIG. 8 is a data processing system in the form of a block diagram in accordance with an illustrative embodiment.

Turning now to FIG. 8, an illustration of a data processing system in the form of a block diagram is depicted in accordance with an illustrative embodiment. Data processing system 800 may be used to implement at least one of model generator 148 or one or more computers in computer system 150 in FIG. 1. As depicted, data processing system 800 includes communications framework 802, which provides communications between processor unit 804, storage devices 806, communications unit 808, input/output unit 810, and display 812. In some cases, communications framework 802 may be implemented as a bus system.

Processor unit 804 is configured to execute instructions for software to perform a number of operations. Processor unit 804 may comprise a number of processors, a multi-processor core, and/or some other type of processor, depending on the implementation. In some cases, processor unit 804 may take the form of a hardware unit, such as a circuit system, an application specific integrated circuit (ASIC), a programmable logic device, or some other suitable type of hardware unit.

Instructions for the operating system, applications, and/or programs run by processor unit 804 may be located in storage devices 806. Storage devices 806 may be in communication with processor unit 804 through communications framework 802. As used herein, a storage device, also referred to as a computer readable storage device, is any piece of hardware capable of storing information on a temporary and/or permanent basis. This information may include, but is not limited to, data, program code, and/or other information.

Memory 814 and persistent storage 816 are examples of storage devices 806. Memory 814 may take the form of, for example, a random access memory or some type of volatile or non-volatile storage device. Persistent storage 816 may comprise any number of components or devices. For example, persistent storage 816 may comprise a hard drive, a flash memory, a rewritable optical disk, a rewritable magnetic tape, or some combination of the above. The media used by persistent storage 816 may or may not be removable.

Communications unit 808 allows data processing system 800 to communicate with other data processing systems and/or devices. Communications unit 808 may provide communications using physical and/or wireless communications links.

Input/output unit 810 allows input to be received from and output to be sent to other devices connected to data processing system 800. For example, input/output unit 810 may allow user input to be received through a keyboard, a mouse, and/or some other type of input device. As another example, input/output unit 810 may allow output to be sent to a printer connected to data processing system 800.

Further, in some illustrative examples, data processing system 800 may include a data acquisition unit. This data acquisition unit may be part of or separate from input/output unit 810, depending on the implementation. The data acquisition unit may be configured to receive data from, for example, without limitation, array of elements 120 in FIG. 1. In particular, the data acquisition unit may be configured to receive layer data 130 from array of elements 120 in FIG. 1.

Display 812 is configured to display information to a user. Display 812 may comprise, for example, without limitation, a monitor, a touch screen, a laser display, a holographic display, a virtual display device, and/or some other type of display device.

In this illustrative example, the processes of the different illustrative embodiments may be performed by processor unit 804 using computer-implemented instructions. These instructions may be referred to as program code, computer usable program code, or computer readable program code and may be read and executed by one or more processors in processor unit 804.

In these examples, program code 818 is located in a functional form on computer readable media 820, which is selectively removable, and may be loaded onto or transferred to data processing system 800 for execution by processor unit 804. Program code 818 and computer readable media 820 together form computer program product 822. In this illustrative example, computer readable media 820 may be computer readable storage media 824 or computer readable signal media 826.

Computer readable storage media 824 is a physical or tangible storage device used to store program code 818 rather than a medium that propagates or transmits program code 818. Computer readable storage media 824 may be, for example, without limitation, an optical or magnetic disk or a persistent storage device that is connected to data processing system 800.

Alternatively, program code 818 may be transferred to data processing system 800 using computer readable signal media 826. Computer readable signal media 826 may be, for example, a propagated data signal containing program code 818. This data signal may be an electromagnetic signal, an optical signal, and/or some other type of signal that can be transmitted over physical and/or wireless communications links.

The illustration of data processing system 800 in FIG. 8 is not meant to provide architectural limitations to the manner in which the illustrative embodiments may be implemented. The different illustrative embodiments may be implemented in a data processing system that includes components in addition to or in place of those illustrated for data processing system 800. Further, components shown in FIG. 8 may be varied from the illustrative examples shown.

The flowcharts and block diagrams in the different depicted embodiments illustrate the architecture, functionality, and operation of some possible implementations of apparatuses and methods in an illustrative embodiment. In this regard, each block in the flowcharts or block diagrams may represent a module, a segment, a function, and/or a portion of an operation or step.

In some alternative implementations of an illustrative embodiment, the function or functions noted in the blocks may occur out of the order noted in the figures. For example, in some cases, two blocks shown in succession may be executed substantially concurrently, or the blocks may sometimes be performed in the reverse order, depending upon the functionality involved. Also, other blocks may be added in addition to the illustrated blocks in a flowchart or block diagram.

The description of the different illustrative embodiments has been presented for purposes of illustration and description, and is not intended to be exhaustive or limited to the embodiments in the form disclosed. Many modifications and variations will be apparent to those of ordinary skill in the art. Further, different illustrative embodiments may provide different features as compared to other desirable embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. A method for evaluating an object, the method comprising:
   identifying a wrinkle axis along which a wrinkle in the object extends;
   positioning a linear array of elements over the wrinkle in a direction substantially perpendicular to the wrinkle axis, wherein the linear array of elements comprises an array of transmitting elements and an array of receiving elements;
   sending, by an ultrasonic inspection system, an ultrasonic beam into the object at each of a plurality of locations using a portion of the array of transmitting elements;
   receiving, by the ultrasonic inspection system, reflected energy the an array of receiving elements in response to a portion of the energy being reflected off a plurality of layers in the object;
   creating a three-dimensional model of a wrinkle in the object based on the reflected energy received at the array of receiving elements; and
   evaluating the object based on the three-dimensional model, wherein evaluating the object includes determining the impact of the wrinkle on mechanical properties of the object.

2. The method of claim 1, wherein receiving the reflected energy at the array of receiving elements comprises:

receiving reflections of the ultrasonic beam at a portion of the array of receiving elements in response to the ultrasonic beam being sent into the object at a location in the plurality of locations;

identifying a plurality of reflected signals corresponding to the plurality of layers in the object and the location based on the reflections; and identifying a receiving element in the portion of the array of receiving elements that receives a highest-amplitude reflected signal of the plurality of reflected signals.

3. The method of claim 2 further comprising:

generating location data for each location in the plurality of locations, wherein generating the location data for the location includes:

identifying a time of arrival of the highest-amplitude reflected signal at the receiving element; and identifying an angle of reflection for the reflected signal based on a location along the linear array of elements of the portion of the array of transmitting elements sending energy into the object, a transmitting angle at which the portion of the array of transmitting elements sends energy into the object, the location along the linear array of elements of the receiving element, and time of arrival of the highest-amplitude reflected signal at the receiving element.

4. The method of claim 3, wherein creating the three-dimensional model of the wrinkle comprises:

generating depth data by identifying a depth for a surface of each of the plurality of layers at the each of the plurality of locations based on the time value and the angle of reflection for the location.

5. The method of claim 4, wherein creating the three-dimensional model of the wrinkle further comprises:

generating three-dimensional data about the wrinkle in the object using the depth data.

6. The method of claim 1, wherein sending the ultrasonic beam into the object at the each of the plurality of locations comprises:

sending the ultrasonic beam into the object at a location in the plurality of locations; and sweeping the ultrasonic beam across a range of angles selected for the location using the portion of the array of transmitting elements, wherein the range of angles is relative to one of a plane through the object and the array of transmitting elements.

7. The method of claim 1, wherein creating the three-dimensional model of the wrinkle comprises:

generating three-dimensional data about the wrinkle in the object based on the reflected energy received.

8. The method of claim 7, wherein generating the three-dimensional data about the wrinkle in the object using the reflected energy comprises:

generating the three-dimensional data about the wrinkle in the object using the reflected energy for use in quantifying a shape and a size of the wrinkle.

9. The method of claim 1 further comprising:

performing a stress analysis for the object using the three-dimensional model of the wrinkle in the object to determine an impact of the wrinkle on a stiffness of the object.

10. An apparatus comprising:

an array of transmitting elements configured to send energy into a plurality of locations on an object;

an array of receiving elements configured to receive at least a portion of the energy that is reflected off the object as reflected energy;

a processor unit configured to:

identify a receiving element in the portion of the array of receiving elements that receives a highest-amplitude reflected signal of the plurality of reflected signals; and generate location data for each of the plurality of locations based on the reflected energy, wherein generating the location data for the location includes: identifying a time of arrival of the highest-amplitude reflected signal at the receiving element; and identifying an angle of reflection for the reflected signal based on a location along the linear array of elements of the portion of the array of transmitting elements sending energy into the object, a transmitting angle at which the portion of the array of transmitting elements sends energy into the object, the location along the linear array of elements of the receiving element, and time of arrival of the highest-amplitude reflected signal at the receiving element; and a model generator configured to create a three-dimensional model of a wrinkle in the object based on the reflected energy.

11. The apparatus of claim 10, wherein the energy is ultrasonic energy.

12. The apparatus of claim 10, wherein the array of receiving elements and the array of transmitting elements are a same array of elements that form a linear array of elements.

13. The apparatus of claim 12, wherein the same array of elements is an array of ultrasonic transducers.

14. The apparatus of claim 10, wherein the three-dimensional model comprises three-dimensional data about the wrinkle.

15. The apparatus of claim 14, wherein the three-dimensional data about the wrinkle is used to determine a size and a shape of the wrinkle.

16. The apparatus of claim 14, wherein the three-dimensional data is used to perform a stress analysis of the object having the wrinkle.

17. The apparatus of claim 10, wherein the object is a composite object comprised of a plurality of composite layers.

18. An ultrasonic inspection system comprising:

an array of transmitting elements configured to send an ultrasonic beam into a composite object at each of a plurality of locations on the object using a transmitting portion of the array of transmitting elements;

an array of receiving elements configured to receive a plurality of reflected signals corresponding to a plurality of layers in the composite object in response to the ultrasonic beam being sent into the composite object at a location in the plurality of locations;

a processor unit configured to:

identify a receiving element in the portion of the array of receiving elements that receives a highest-amplitude reflected signal of the plurality of reflected signals; and generate location data for each of the plurality of locations based on the reflected energy, wherein generating the location data for the location includes: identifying a time of arrival of the highest-amplitude reflected signal at the receiving element; and identifying an angle of reflection for the reflected signal based on a location along the linear array of elements of the portion of the array of transmitting elements sending energy into the object, a transmitting angle at which the portion of the array of transmitting elements sends energy into the object, the location along the linear array of elements of the receiving element, and time of arrival of the highest-amplitude reflected signal at the receiving element; and a model generator configured to create a three-dimensional model of a wrinkle in the composite object based on the plurality of reflected signals received for each location in the plurality of locations, wherein the three-dimensional model is used to determine a size and a shape of the wrinkle.

* * * * *

UNITED STATES PATENT AND TRADEMARK OFFICE
CERTIFICATE OF CORRECTION

PATENT NO.        : 9,575,033 B1
APPLICATION NO.   : 14/049974
DATED             : February 21, 2017
INVENTOR(S)       : Georgeson et al.

It is certified that error appears in the above-identified patent and that said Letters Patent is hereby corrected as shown below:

In the Claims

Column 14, Line 56, herein change, "the an array" to read as -the array-

Signed and Sealed this
Thirtieth Day of April, 2019

Andrei Iancu
*Director of the United States Patent and Trademark Office*